United States Patent
Pouzet et al.

(10) Patent No.: US 6,660,772 B2
(45) Date of Patent: Dec. 9, 2003

(54) USE OF 2-AMINO-1-(4-HYDROXY-2-METHANESULFONAMIDOPHENYL) ETHANOL FOR TREATING URINARY INCONTINENCE

(75) Inventors: Pascale Pouzet, Biberach (DE); Franz Esser, Ingelheim (DE); Hisato Kitagawa, Osaka (JP); Naoki Ishiguro, Osaka (JP); Ikunobu Muramatsu, Fukui (JP)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/060,492

(22) Filed: Jan. 30, 2002

(65) Prior Publication Data
US 2002/0169213 A1 Nov. 14, 2002

Related U.S. Application Data
(60) Provisional application No. 60/270,303, filed on Feb. 20, 2001.

(30) Foreign Application Priority Data
Feb. 1, 2001 (DE) .......................... 101 04 369

(51) Int. Cl.$^7$ .................. A61K 514/605; C07C 564/99
(52) U.S. Cl. .......................................... 514/605; 564/99
(58) Field of Search ............................. 514/605; 564/99

(56) References Cited

U.S. PATENT DOCUMENTS
3,341,584 A  9/1967  Larsen et al.

FOREIGN PATENT DOCUMENTS

| EP | 0 538 469 B1 | 4/1993 |
| EP | 0 538 469 A1 | 4/1993 |
| WO | WO 96/32939 | 10/1996 |
| WO | WO 00/10557 | 3/2000 |

OTHER PUBLICATIONS

Leoni et al., Chem. Abst. 79:179 (1973).
Larsen, A.A. et al; "Sulfonanilides. II. Analogs of Catecholamines 1,2"; Journal of Medicinal Chemistry; 1967; 462–472; vol. 10.
Chemical Abstracts 126:195005 (1997); Taniguchi, N. et al; NS–49, an a1A–adrenoceptor agonist, selectively increases intraurethral pressure in dogs, European Journal of Pharmacology (1996), 318 (1), 117, 122.

*Primary Examiner*—Peter O'Sullivan
(74) *Attorney, Agent, or Firm*—R. P. Raymond; T. X. Witkowski

(57) ABSTRACT

A method of treating urinary incontinence in a patient in need thereof, the method comprising administering to the patient an effective amount of 2-amino-1-(4-hydroxy-2-methanesulfonamidophenyl)ethanol or a pharmacologically acceptable salt thereof, and pharmaceutical compositions.

48 Claims, No Drawings

USE OF 2-AMINO-1-(4-HYDROXY-2-METHANESULFONAMIDOPHENYL) ETHANOL FOR TREATING URINARY INCONTINENCE

RELATED APPLICATIONS

Benefit under 35 U.S.C. §119(e) of prior provisional application Serial No. 60/270,303, filed Feb. 20, 2001, is hereby claimed.

BACKGROUND OF THE INVENTION

The present invention relates to medicaments containing 2-amino-1-(4-hydroxy-3-methanesulfonamidophenyl) ethanol, one of the two optical isomers thereof, and/or the pharmacologically acceptable salts thereof, particularly for treating urinary incontinence.

The compound according to the invention has the following structure (Formula (I)).

By incontinence is meant an involuntary release of urine, i.e., weakness of the bladder. The various manifestations of urinary incontinence include urge incontinence, reflex incontinence, overflow incontinence, and stress incontinence. The most common form of urinary incontinence is stress incontinence. Women, in particular, are affected by this after more or less difficult childbirth. The reason for this is that pregnancy and labor easily lead to a weakening of the pelvic floor. Other causes of incontinence may lie, for example, in damage to the nerves of the pelvic floor, a congenitally short urethra, or damage to the sphincter muscle.

According to WO 96/32939 it is beneficial to use alpha-1L-agonists in the treatment of urinary incontinence, as they act selectively on the adrenoreceptors of the bladder and thus have a crucial effect on the tonicity of the urethra, without significantly affecting the cardiac circulatory system.

EP 0 538 469 describes 2-amino-1-(2-fluoro-5-methanesulfonamidophenyl)ethanol and the use thereof for treating urinary incontinence.

SUMMARY OF THE INVENTION

Surprisingly, it has now been found that the compound of Formula (I) has an outstanding agonistic effect on alpha-1L-receptors. The substance acts highly selectively on the bladder and inhibits urinary urgency.

The aim is therefore to develop a medicament with which urinary incontinence can be treated in a controlled manner.

A further objective is to develop medicaments which act selectively on the contractile mechanisms of the bladder without seriously affecting other organs such as, e.g., peripheral blood vessels.

Another objective is to develop a medicament for treating urinary incontinence, in particular stress urinary incontinence, which has a relatively long-lasting effect.

Another objective is to develop a method of treating urinary incontinence, in particular stress urinary incontinence.

Preferably, a drug which can be administered orally should be developed.

A further aim is to develop a non-toxic drug with few side-effects.

The overall aim of the present invention is therefore to find an active substance having the profiles described above and to develop a suitable medicament therefrom.

DETAILED DESCRIPTION OF THE INVENTION

The racemate of the compound according to the invention has been known since the 1960s. It is described, for example, in U.S. Pat. No. 3,341,584 and GB 933,584. These publications mention that the racemate has a stimulant effect on alpha- and/or beta-receptors. The Journal of Medicinal Chemistry 1967, 10, page 467, describes an alpha-adrenergic effect.

The enantiomerically pure forms of the compound, i.e., the R- or S-form, are not known as pharmaceutical substances. Furthermore, the use of the compound as a racemate or in enantiomerically pure form, i.e., in the R- or S-form, in a pharmaceutical composition for treating urinary incontinence, in particular stress urinary incontinence, is not known.

The compound is used in a pharmaceutical composition in the form of the racemate or one of the pure enantiomers.

The substance may be used both as a free base and as an acid addition salt. Examples of such salts are salts of inorganic acids such as hydrochloric acid, hydrobromic acid, sulfuric acid, or phosphoric acid, or organic acids such as acetic acid, citric acid, tartaric acid, malic acid, succinic acid, fumaric acid, p-toluenesulfonic acid, benzenesulfonic acid, methanesulfonic acid, lactic acid, ascorbic acid, etc. The hydrochloride is preferably used.

The compound according to the invention may be administered as a medicament by inhalation, orally, intranasally, intravenously, subcutaneously, intramuscularly, transdermally, or vaginally, or as a suppository. Oral administration is preferred.

The compound may be administered on its own or in conjunction with other appropriate active substances.

To determine the optimum dose of the active substance for urinary incontinence, various parameters have to be taken into consideration, such as the age and body weight of the patient, and the nature and stage of the complaint.

The preferred dose for humans is between 0.001 mg and 1 g per day, preferably between 0.001 mg and 500 mg, more preferably between 0.01 mg and 100 mg, and most preferably between 0.01 mg and 10 mg.

In some cases a smaller amount may be sufficient, whereas in other cases a larger total amount may be needed.

The total daily dose may be taken in one go or in several portions depending on the treatment regimen. The treatment regimen may also prescribe intervals of more than one day between doses of the drug.

The active substance according to the invention may be administered orally in various formulations, e.g., as a solid, in liquid form, as a powder, in the form of tablets, as a coated tablet, sugar-coated tablets, as an oral disintegrating tablet, as a sublingual tablet, in a capsule, in granulated form, as a suspension, solution, emulsion, elixir, or syrup, in the form of drops or in other forms.

Capsules may be produced, starting from a powder of the kind mentioned above or other powders, which are packed into a capsule, preferably a gelatine capsule.

It is also possible to introduce lubricants known from the prior art into the capsule or to use them to seal the two halves of the capsule. The dissolution rate of a capsule can be increased by the addition of disintegrant or solubilizing substances, such as, for example, carboxymethylcellulose, carboxymethylcellulose calcium, lowly-substituted hydroxypropylcellulose, calcium carbonate, sodium carbonate, sodium carboxymethyl starch, crospovidone, croscarmellose sodium and other substances. The active substance may be contained in the capsule not only as a solid but also in solution or in suspension, e.g., in vegetable oil, polyethyleneglycol, or glycerol, using surfactants, etc.

Tablets (including vaginal tablets) may be prepared in which the powdered mixture is processed to form granules, mixed with other substances if necessary, and then further compressed, for example. The tablets may contain various excipients, e.g., starches, lactose, sucrose, glucose, sodium chloride, urea for soluble or injectable tablets, amylose, various types of cellulose as described above, etc. Glycerol or starch may be added, for example, as moisture retaining agents.

Starch, alginic acid, calcium alginate, pectic acid, powdered agar—agar, formaldehyde gelatine, calcium carbonate, sodium bicarbonate, magnesium peroxide, and amylose, for example, may be used as disintegrants.

Sucrose, stearin, solid paraffin (preferably with a melting point in the range from 50° C.-52° C.), cocoa butter, and hydrogenated fats may be used as anti-disintegrants or solution retardants.

Suitable resorption accelerators include, inter alia, quaternary ammonium compounds, sodium lauryl sulfate, saponins.

Ether may be used as a binder distributor, for example, and cetyl alcohol, glycerol monostearate, starch, lactose, wetting agents (e.g., Aerosol OT, Pluronics, Tweens), etc. may be used as hydrophilizers or breakdown accelerators Moreover, the following may be considered as tablet-making excipients in general: Aerosil, Aerosol OT ethylcellulose, Amberlite resin, XE-88, Amijel, Amisterol, amylose, Avicel microcrystalline-cellulose, bentonite, calcium sulfate, Carbowax 4000 and 6000, carrageenin, castor wax, cellulose, microcrystalline cellulose, dextran, dextrin, base for pharmaceutical tablets, kaolin, spray dried lactose (USP), lactosil, magnesium stearate, mannitol, mannitol granular N.F. methylcellulose, Miglyol 812 neutral oil, powdered milk, lactose, nal-tab, Nepol-amylose, Pöfizer crystalline sorbitol, plasdone, polyethyleneglycols, polyvinylpyrrolidone, Précirol, calves' foot oil (hydrogenated), base for melting tablets, silicones, stabiline, Sta-rx 1500, Syloid, Waldhof tablet base, Tablettol, talcum cetylatum and stearatum, Tego metal soaps, dextrose, and tylose. The tabletting adjuvant K (M25) is particularly preferred and also meets the requirements of the following pharmacopoeias: DAB, Ph, Eur, BP, and NF.

Other excipients from the prior art may also be used.

The tablets may be produced by direct compression.

Other formulations suitable for oral administration may also be prepared, such as suspensions, solutions, emulsions, syrups, elixirs, etc. If desired, the compound may be microencapsulated.

A powder may be prepared, for example, by reducing the particles of active substance to a suitable size by grinding.

Diluted powders may be prepared by finely grinding the powdered substance with a non-toxic carrier such as lactose and producing it as a powder. Other carrier materials which are suitable for this purpose are other carbohydrates such as starch or mannitol. If desired, these powders may contain flavorings, preservatives, dispersants, colorings, and other pharmaceutically excipients.

The compound may be administered parenterally by dissolving, emulsifying, or suspending it in a liquid and injecting it by subcutaneous, intramuscular, or intravenous route. Suitable solvents include, for example, water or oily media.

To prepare suppositories the compound may be formulated with low-melting and water-soluble or water-insoluble materials such polyethyleneglycol, cocoa butter, higher esters (e.g., myristyl palmitate), or mixtures thereof.

EXAMPLES

1. Metabolism

To determine the metabolism the enzyme CYP2D6 was allowed to act on the hydrochloride of the compound 1 according to the invention. After 30 minutes, a check was made to determine how much of the substance had been broken down by the enzyme. (−)-R-2-Amino-1-(2-fluoro-5-methanesulfonamidophenyl)ethanol 2 was used as a comparison.

| Compound | % Substrate Breakdown After 30 minutes' Incubation with CYP2D6 |
|---|---|
| 1 | 1.4 |
| 2 | 2.1 |

2. Efficacy and Selectivity

The efficacy and selectivity of the compound according to the invention is determined as follows, using the same findings as described in 1:

| Compound | Activity in the Dog | Activity on Human Urethra | Selectivity in the Dog |
|---|---|---|---|
| 1 | 103 | 120 | 53 |
| 2 | 79 | 48 | 40 |

Maximum contraction in the dog and activity on human urethra are percentages of contraction compared with noradrenaline. Selectivity in the dog is the difference obtained from the percentage contraction of the dog's femoral artery at $10^{-5}$ M and percentage contraction of the carotid artery in the dog at $10^{-5}$ M.

3. Pharmaceutical Compositions

Example A Tablets

| | |
|---|---|
| 2-amino-1-(4-hydroxy-3-methanesulfonamidophenyl)ethanol | 1 mg |
| Lactose | 105 mg |
| Microcrystalline cellulose | 30 mg |
| Corn starch | 30 mg |
| Povidone | 5 mg |
| Sodium carboxymethyl starch | 5 mg |

-continued

| | |
|---|---|
| Colloidal silica | 3 mg |
| Magnesium stearate | 1 mg |
| Total | 180 mg |

Preparation: The active substance is mixed with some of the excipients and granulated in the usual way. The granules are sieved, combined with the remaining excipients and compressed into tablets weighing 180 mg.

Example B Ampoules

| | |
|---|---|
| 2-amino-1-(4-hydroxy-3-methanesulfonamidophenyl)ethanol | 1.0 mg |
| Sodium chloride | 18.0 mg |
| Sufficient water for injection to make up to 2.0 mL | |

Preparation: The active substance and sodium chloride are dissolved in water for injection and transferred into glass ampoules in an aseptic condition.

Example C Capsules

| | |
|---|---|
| 2-amino-1-(4-hydroxy-3-methanesulfonamidophenyl)ethanol | 1 mg |
| Lactose | 178 mg |
| Magnesium stearate | 1 mg |
| Total | 180 mg |

Preparation: The active substance is mixed with the excipients and filled into capsules as known in the state of the art.

Preparation of the Racemic Compound

The racemic compound can be prepared according to the procedures disclosed in GB 993,584 or U.S. Pat. No. 3,341,584.

Preparation of the Enantiomerically Pure Forms

The pure enantiomers of the compound of the present invention can be obtained, for example, by transforming them into an diastereomeric salt, for example, with tartaric acid or other acids as mentioned above, followed by separating the two diastereomeric salts from each other via crystallisation and then liberating the pure enantiomer as the free base by adding a strong amino base or an alkali hydroxide.

Another way to obtain the pure enantiomers is by purifying the racemate via HPLC by using a chiral column. Yet another way to obtain the pure enantiomers is by transforming the racemic mixture into diastereomers, for example, the diastereomeric salts as described above, to separate the two different diastereomers as diastereomeric salts and then to liberate the pure enantiomer again.

All separation procedures as such are well known in the art.

We claim:

1. A method of treating urinary incontinence in a patient in need thereof, the method comprising administering to the patient an effective amount of 2-amino-1-(4-hydroxy-3methanesulfonamidophenyl)ethanol or a pharmacologically acceptable salt thereof.

2. The method according to claim 1, wherein the method comprises administering to the patient an effective amount of R-2-amino-1-(4-hydroxy-3-methanesulfonamidophenyl) ethanol or a pharmacologically acceptable salt thereof.

3. The method according to claim 1, wherein the method comprises administering to the patient an effective amount of S-2-amino-1-(4-hydroxy-3-methanesulfonamidophenyl) ethanol or a pharmacologically acceptable salt thereof.

4. The method according to claim 2, wherein no S-2-amino-1-(4-hydroxy-3-methanesulfonamidophenyl)ethanol or a pharmacologically acceptable salt thereof is administered to the patient.

5. The method according to claim 3, wherein no R-2-amino-1-(4-hydroxy-3-methanesulfonamidophenyl)ethanol or a pharmacologically acceptable salt thereof is administered to the patient.

6. The method according to claim 1, wherein the method comprises administering to the patient an effective amount of the racemate of 2-amino-1-(4-hydroxy-3-methanesulfonamidophenyl)ethanol or a pharmacologically acceptable salt thereof.

7. The method according to claim 1, wherein the pharmacologically acceptable salt is a hydrochloride salt.

8. The method according to claim 2, wherein the pharmacologically acceptable salt is a hydrochloride salt.

9. The method according to claim 3, wherein the pharmacologically acceptable salt is a hydrochloride salt.

10. The method according to claim 4, wherein the pharmacologically acceptable salt is a hydrochloride salt.

11. The method according to claim 5, wherein the pharmacologically acceptable salt is a hydrochloride salt.

12. The method according to claim 6, wherein the pharmacologically acceptable salt is a hydrochloride salt.

13. The method according to claim 1, wherein the effective amount is between 0.001 mg and 1 g.

14. The method according to claim 2, wherein the effective amount is between 0.001 mg and 1 g.

15. The method according to claim 3, wherein the effective amount is between 0.001 mg and 1 g.

16. The method according to claim 4, wherein the effective amount is between 0.001 mg and 1 g.

17. The method according to claim 5, wherein the effective amount is between 0.001 mg and 1 g.

18. The method according to claim 6, wherein the effective amount is between 0.001 mg and 1 g.

19. The method according to claim 13, wherein the effective amount is between 0.001 mg and 100 mg.

20. The method according to claim 14, wherein the effective amount is between 0.001 mg and 100 mg.

21. The method according to claim 15, wherein the effective amount is between 0.001 mg and 100 mg.

22. The method according to claim 16, wherein the effective amount is between 0.001 mg and 100 mg.

23. The method according to claim 17, wherein the effective amount is between 0.001 mg and 100 mg.

24. The method according to claim 18, wherein the effective amount is between 0.001 mg and 100 mg.

25. The method according to claim 19, wherein the effective amount is between 0.01 mg and 10 mg.

26. The method according to claim 20, wherein the effective amount is between 0.01 mg and 10 mg.

27. The method according to claim 21, wherein the effective amount is between 0.01 mg and 10 mg.

28. The method according to claim 22, wherein the effective amount is between 0.01 mg and 10 mg.

29. The method according to claim 23, wherein the effective amount is between 0.01 mg and 10 mg.

30. The method according to claim 24, wherein the effective amount is between 0.01 mg and 10 mg.

31. The method according to claim 1, wherein the 2-amino-1-(4-hydroxy-3-methanesulfonamidophenyl) ethanol or a pharmacologically acceptable salt thereof is administered to the patient orally.

32. The method according to claim 2, wherein the 2-amino-1-(4-hydroxy-3-methanesulfonamidophenyl) ethanol or a pharmacologically acceptable salt thereof is administered to the patient orally.

33. The method according to claim 3, wherein the 2-amino-1-(4-hydroxy-3-methanesulfonamidophenyl) ethanol or a pharmacologically acceptable salt thereof is administered to the patient orally.

34. The method according to claim 4, wherein the 2-amino-1-(4-hydroxy-3-methanesulfonamidophenyl) ethanol or a pharmacologically acceptable salt thereof is administered to the patient orally.

35. The method according to claim 5, wherein the 2-amino-1-(4-hydroxy-3-methanesulfonamidophenyl) ethanol or a pharmacologically acceptable salt thereof is administered to the patient orally.

36. The method according to claim 6, wherein the 2-amino-1-(4-hydroxy-3-methanesulfonamidophenyl) ethanol or a pharmacologically acceptable salt thereof is administered to the patient orally.

37. The method according to claim 1, wherein the 2-amino-1-(4-hydroxy-3-methanesulfonamidophenyl) ethanol or a pharmacologically acceptable salt thereof is administered to the patient transdermally, parenterally, rectally, or vaginally.

38. The method according to claim 2, wherein the 2-amino-1-(4-hydroxy-3-methanesulfonamidophenyl) ethanol or a pharmacologically acceptable salt thereof is administered to the patient transdermally, parenterally, rectally, or vaginally.

39. The method according to claim 3, wherein the 2-amino-1-(4-hydroxy-3-methanesulfonamidophenyl) ethanol or a pharmacologically acceptable salt thereof is administered to the patient transdermally, parenterally, rectally, or vaginally.

40. The method according to claim 4, wherein the 2-amino-1-(4-hydroxy-3-methanesulfonamidophenyl) ethanol or a pharmacologically acceptable salt thereof is administered to the patient transdermally, parenterally, rectally, or vaginally.

41. The method according to claim 5, wherein the 2-amino-1-(4-hydroxy-3-methanesulfonamidophenyl) ethanol or a pharmacologically acceptable salt thereof is administered to the patient transdermally, parenterally, rectally, or vaginally.

42. The method according to claim 6, wherein the 2-amino-1-(4-hydroxy-3-methanesulfonamidophenyl) ethanol or a pharmacologically acceptable salt thereof is administered to the patient transdermally, parenterally, rectally, or vaginally.

43. A pharmaceutical composition comprising:
   (a) R-2-amino-1-(4-hydroxy-3-methanesulfonamidophenyl)ethanol or a pharmacologically acceptable salt thereof; and
   (b) pharmaceutically acceptable excipient.

44. A pharmaceutical composition comprising:
   (a) S-2-amino-1-(4-hydroxy-3-methanesulfonamidophenyl)ethanol or a pharmacologically acceptable salt thereof; and
   (b) pharmaceutically acceptable excipient.

45. The pharmaceutical composition according to claim 43, wherein the pharmacologically acceptable salt is a hydrochloride salt.

46. The pharmaceutical composition according to claim 44, wherein the pharmacologically acceptable salt is a hydrochloride salt.

47. The pharmaceutical composition according to claim 43, wherein the pharmaceutical composition is a tablet or capsule.

48. The pharmaceutical composition according to claim 44, wherein the pharmaceutical composition is a tablet or capsule.

* * * * *